(12) United States Patent
Matthews

(10) Patent No.: US 9,939,714 B1
(45) Date of Patent: Apr. 10, 2018

(54) INTRA-ORAL CAMERA

(71) Applicant: Andrew Ryan Matthews, Redding, CA (US)

(72) Inventor: Andrew Ryan Matthews, Redding, CA (US)

( * ) Notice: Subject to any disclaimer, the term of this patent is extended or adjusted under 35 U.S.C. 154(b) by 0 days.

(21) Appl. No.: 15/471,632

(22) Filed: Mar. 28, 2017

(51) Int. Cl.
| | |
|---|---|
| *G03B 17/56* | (2006.01) |
| *G03B 15/04* | (2006.01) |
| *H04N 5/225* | (2006.01) |
| *F16B 1/00* | (2006.01) |
| *A61B 1/00* | (2006.01) |
| *A61B 1/04* | (2006.01) |
| *A61B 1/06* | (2006.01) |
| *A61B 1/07* | (2006.01) |
| *A61B 1/24* | (2006.01) |
| *A61B 5/00* | (2006.01) |
| *H04M 1/725* | (2006.01) |

(52) U.S. Cl.
CPC ........ *G03B 17/565* (2013.01); *A61B 1/00101* (2013.01); *A61B 1/00105* (2013.01); *A61B 1/00126* (2013.01); *A61B 1/042* (2013.01); *A61B 1/0669* (2013.01); *A61B 1/07* (2013.01); *A61B 1/24* (2013.01); *A61B 5/6898* (2013.01); *F16B 1/00* (2013.01); *G03B 15/04* (2013.01); *G03B 17/561* (2013.01); *H04M 1/72527* (2013.01); *H04N 5/2256* (2013.01); *H04N 5/2259* (2013.01); *F16B 2001/0035* (2013.01); *H04N 2005/2255* (2013.01)

(58) Field of Classification Search
CPC .... G03B 17/56; G03B 11/041; G03B 11/045; A45C 2011/002
See application file for complete search history.

(56) References Cited

U.S. PATENT DOCUMENTS

| | | | |
|---|---|---|---|
| 3,382,781 A | | 5/1968 | Hamilton |
| 4,484,805 A | * | 11/1984 | Gizzio .................. G03B 15/00 396/337 |
| 5,290,168 A | | 3/1994 | Cooper et al. |

(Continued)

FOREIGN PATENT DOCUMENTS

| | | |
|---|---|---|
| CN | 202841268 | 3/2013 |
| CN | 103458165 | 12/2013 |

(Continued)

OTHER PUBLICATIONS

Seaflower Technology Company Limited, 90 Degree Turning Periscope Lens Mobile Phone Camera Lens (A-8022), http://www.made-in-china.com/showroom/hk-seaflower/product-detaili...gree-Turning-Periscope-Lens-Mobile-Phone-Camera-Lens-A-8022-.html; Feb. 28, 2017.

*Primary Examiner* — Minh Phan
(74) *Attorney, Agent, or Firm* — Douglas L. Weller

(57) ABSTRACT

A periscope module includes a mounting ring for mounting the periscope module over a camera lens of a mobile phone. A first periscope end is for attachment to the mobile phone at the mounting ring. A second periscope end is for capturing images. A periscope tube is connected between the first periscope end and the second periscope end. A light tube is configured for attachment to a light source from the mobile phone. The light tube is configured to receive light into the first periscope end, the light exiting the second periscope end so as to provide illumination for capturing intra-oral images.

17 Claims, 5 Drawing Sheets

(56) References Cited

U.S. PATENT DOCUMENTS

| | | | |
|---|---|---|---|
| 5,469,236 A * | 11/1995 | Roessel | G02B 23/08 352/94 |
| 7,104,792 B2 | 9/2006 | Taub et al. | |
| 8,577,212 B2 | 11/2013 | Thiel | |
| 9,325,884 B2 | 5/2016 | Fletcher et al. | |
| 9,454,066 B2 | 9/2016 | O'Neill et al. | |
| 2002/0077069 A1 | 6/2002 | Heurtaux | |
| 2013/0188943 A1* | 7/2013 | Wu | G03B 17/17 396/419 |
| 2013/0330684 A1 | 12/2013 | Dillon et al. | |
| 2015/0172522 A1 | 6/2015 | O'Neill et al. | |
| 2016/0224820 A1 | 8/2016 | Riopka et al. | |
| 2016/0256240 A1 | 9/2016 | Shivapuja et al. | |
| 2016/0346494 A1 | 12/2016 | Harrison | |
| 2016/0370991 A1 | 12/2016 | Itzhaik | |

FOREIGN PATENT DOCUMENTS

| | | |
|---|---|---|
| CN | 104367382 A | 2/2015 |
| CN | 205157878 | 4/2016 |
| WO | WO 2015082300 A1 | 6/2015 |

* cited by examiner

INTRA-ORAL CAMERA

BACKGROUND

Cameras on mobile phones are able to capture photographs and videos. Most cameras on mobile phones have fixed-focus lenses and sensors whose small size limit their performance in poor lighting. Photoflash is often provided by a light-emitting diode (LED) source which illuminates less intensely over a much longer exposure time than a traditional flash strobe.

DESCRIPTION OF THE EMBODIMENT

Figure 1:
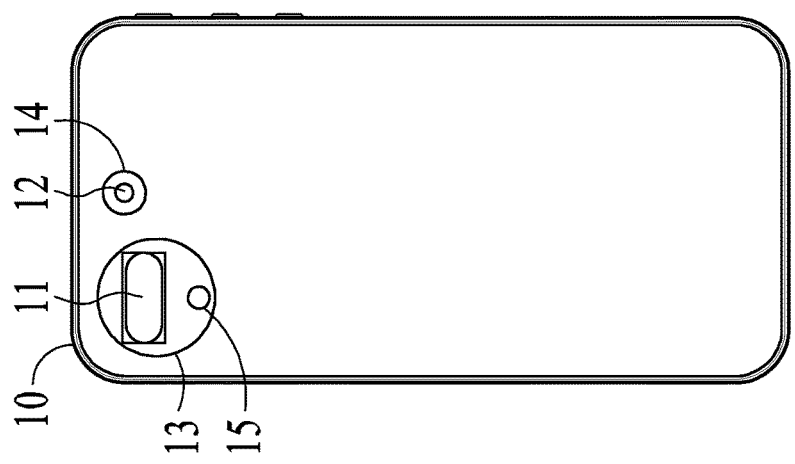
FIG. 1 shows a mobile phone with a camera and LED flash source prepared for mounting a periscope module in accordance with an embodiment.

FIG. 1 shows a mobile phone 10. Around a camera lens 11 is placed a periscope mounting ring 13 with a magnet 15 used to hold a periscope module in place. A ring attachment 14 located around LED light source 12 has a phone adherence portion that adheres to mobile phone 10 and a light tube adherence portion that adheres to a light tube 31, shown in FIG. 3. The light tube adherence portion rotates with respect to the phone adherence portion so that light tube 31 when attached to the light tube adherence portion can rotate with respect to LED light source 12.

Figure 2:
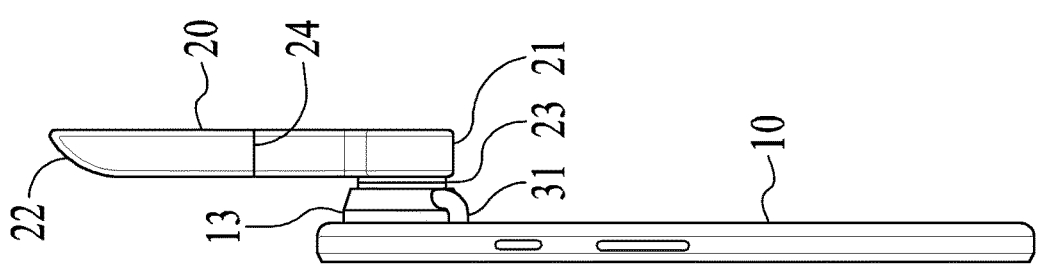
FIG. 2 shows a periscope module mounted on a mobile phone in accordance with an embodiment.

FIG. 2 shows a periscope module 20 mounted on mobile phone 10 at periscope mounting ring 13. Magnet 15 holds periscope module 20 to periscope mounting ring 13, making it simple to attach and detach periscope module 20 to mobile phone 10. A swivel ring 23 allows periscope module 20 to rotate 360 degrees with respect to mounting ring 13. This allows positioning of periscope module 20 when mobile phone 10 and periscope module are used as part of an intra-oral camera. Periscope module 20 includes a periscope reflector 21 and a periscope reflector 22 that directs light within periscope module 20. A swivel point 24 allows swiveling of the periscope 20 to allow adjustment of positioning of periscope reflector 22. This ability to swivel 360 degrees allows a user to rotate to a 90-degree view for a Buccal image, or 180 Degrees for an upper or Maxilla image when using camera 10 and periscope module 20 as an intra-oral camera.

Figure 3:
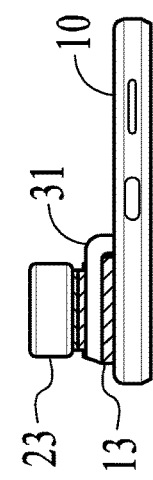
FIG. 3 shows a light tube connected to a periscope module mounted on a mobile phone in accordance with an embodiment.

FIG. 3 shows a top view of mobile phone 10 with swivel ring 23 connected above periscope mounting ring 13. A light tube 31 directs light from LED light source 12 of mobile phone 10 into periscope module 20. This provides illumination that allows mobile phone 10 and periscope module 20 to together act as an intra-oral camera. Light tube 31 is held against LED light source 12 by ring attachment 14.

Figure 4:
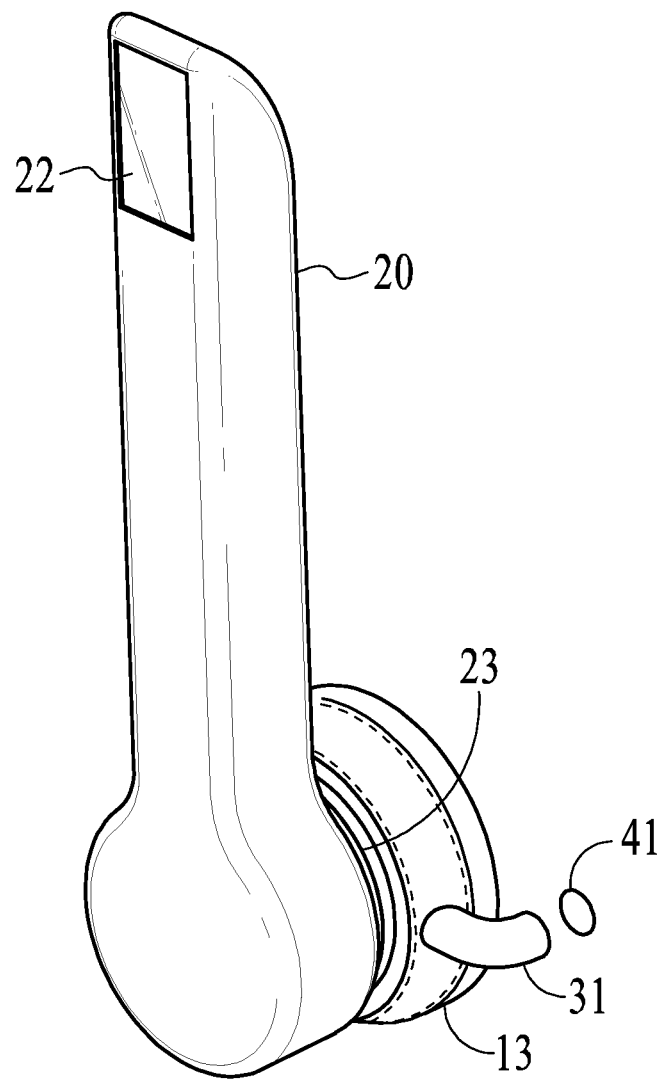
FIG. 4 shows a light tube connected to a periscope module ready to be mounted on a mobile phone in accordance with an embodiment.

FIG. 4 provides another view of periscope module 20 and light tube 31. Light tube 31 enters periscope module 20 between periscope mounting ring 13 and swivel ring 23. Swivel ring 23 is connected above periscope mounting ring 13. Light from LED light source 12 exits periscope module 20 from periscope reflector 22. Light tube 31 is able to rotate around swivel ring 23 to be positioned to accommodate various locations of a LED light source on different types of mobile phones. For example, a clicked swivel embodiment allows locking light tube 31 into position to accommodate a location of a LED light source on a mobile phone. This allows periscope module 20 to be adapted to use on a variety of models of mobile phones available from various manufacturers. A diameter of light tube 31 is selected to be greater than or equal to a diameter of an opening 41 of the light source providing light to light tube 31.

For example, periscope module 20 is constructed by a tube portion 51 located between a 90-degree turning periscope mobile phone camera lens 52 and a 90-degree turning periscope mobile phone camera lens 53. For example, one or both of 90-degree turning periscope mobile phone camera lens 52 and 90-degree turning periscope mobile phone camera lens 53 are implemented from a periscope mobile phone camera lens model A-8022 available from Seaflower Technology Company Limited, in Guangdong, China. For example, periscope mobile phone camera lens 53 is able to swivel 360 degrees with respect to tube portion 51 allowing a user to rotate to a 90-degree view for a Buccal image, or 180 Degrees for an upper or Maxilla image when using camera 10 and periscope module 20 as an intra-oral camera. Rotation is, for example, alternative to, or in addition to swivel point 24. For example, periscope module 20 is made of materials that can be sterilized in an autoclave at or above 132° C. (270° F.) allowing for sterilization when during use periscope module 20 becomes contaminated. In order to allow this, periscope module 20 and other parts used to form the mobile intra-oral camera are made with durable resins and metals that can withstand the heat used for sterilization and that can withstand chemical disinfection surface wipes. For example, a plastic barrier sleeve can be used to cover all or part of periscope module 20 during use to prevent contamination.

Figure 5:
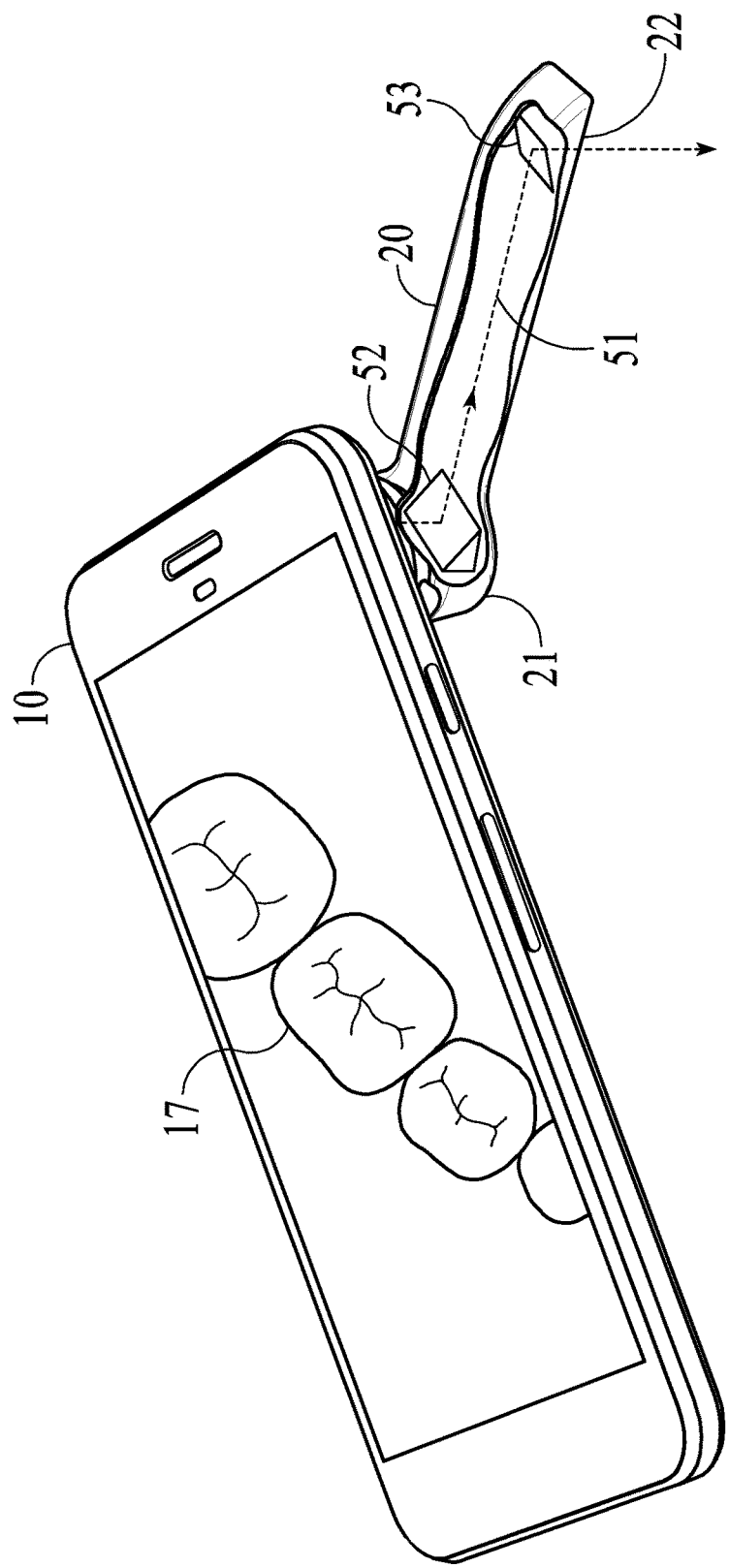
FIG. 5 shows a periscope module mounted on a mobile phone used as an intra-oral camera in accordance with an embodiment.

FIG. 5 illustrates mobile phone 10 and periscope module 20 activing together as an intra-oral camera. Light from LED light source 12 travels through periscope module 20 and provides illumination to teeth in a patient's mouth. A visual image of the teeth returns back through periscope module 20 and is captures by camera lens 11 of mobile phone 10. An image of the teeth is shown on a screen 17 of mobile phone 10. Pictures or video of the teeth can be recorded by mobile phone 10. For example, an intra-oral camera app is response to voice commands such as "snap picture", "start video", "stop video", "increase light", "decrease light" and so on.

For the purposes of illustration, periscope module 20 has been shown to have a fairly straightforward configuration. However, depending on application requirements, periscope module 20 can use any configuration convenient for implementing an intra-oral camera.

Figure 6:
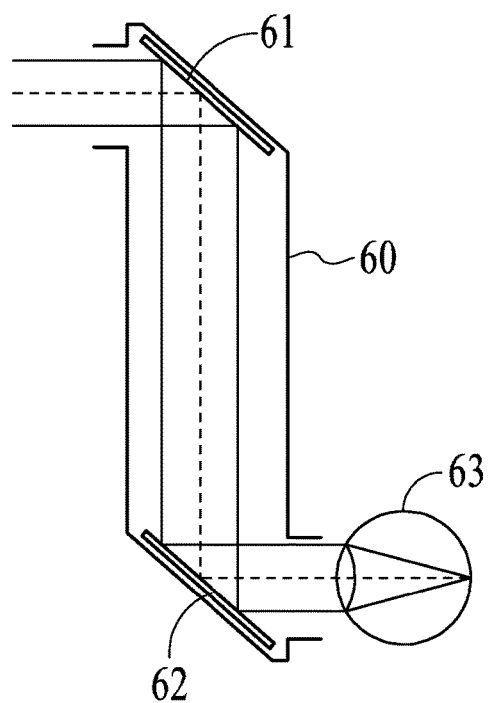
FIG. 6, FIG. 7, FIG. 8 and FIG. 9 show various configurations of a periscope that can be used with an intra-oral camera.

For example, FIG. 6 shows a periscope 60 implemented using a mirror reflector 61 and a mirror reflector 62 to focus an image at a camera lens location 63.

Figure 7:
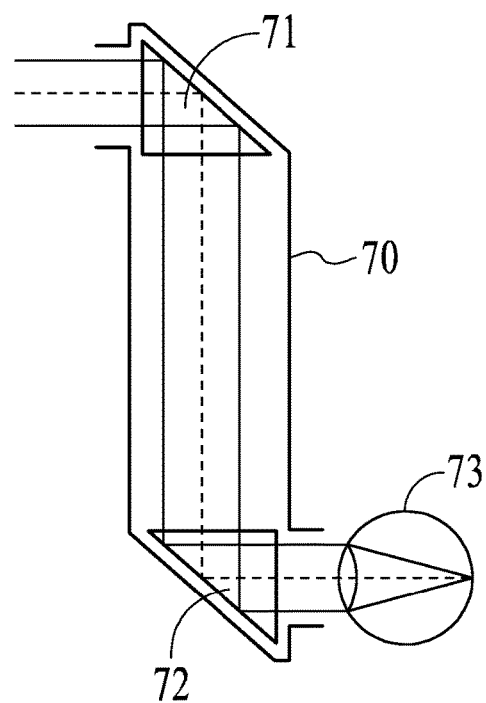
Figure 8:
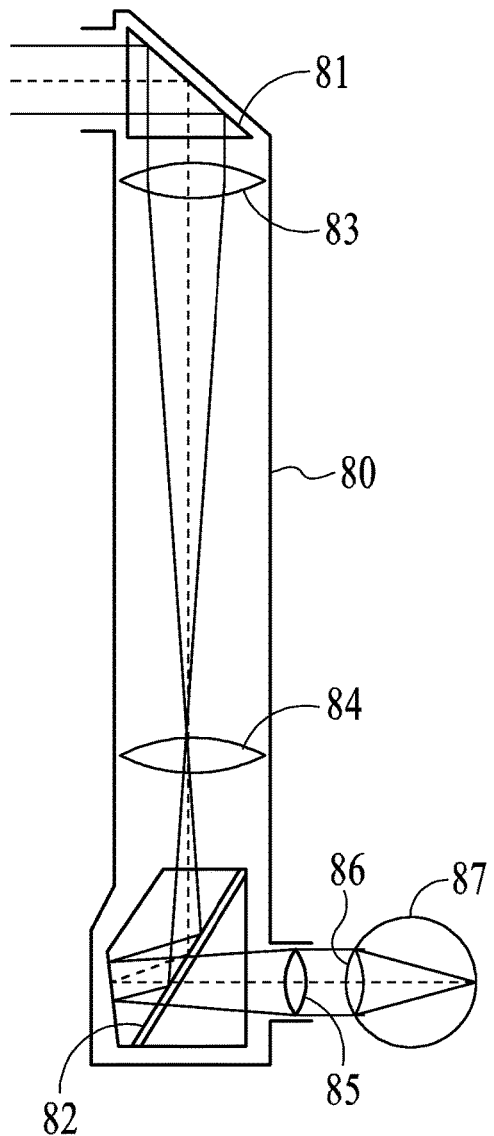
Figure 9:
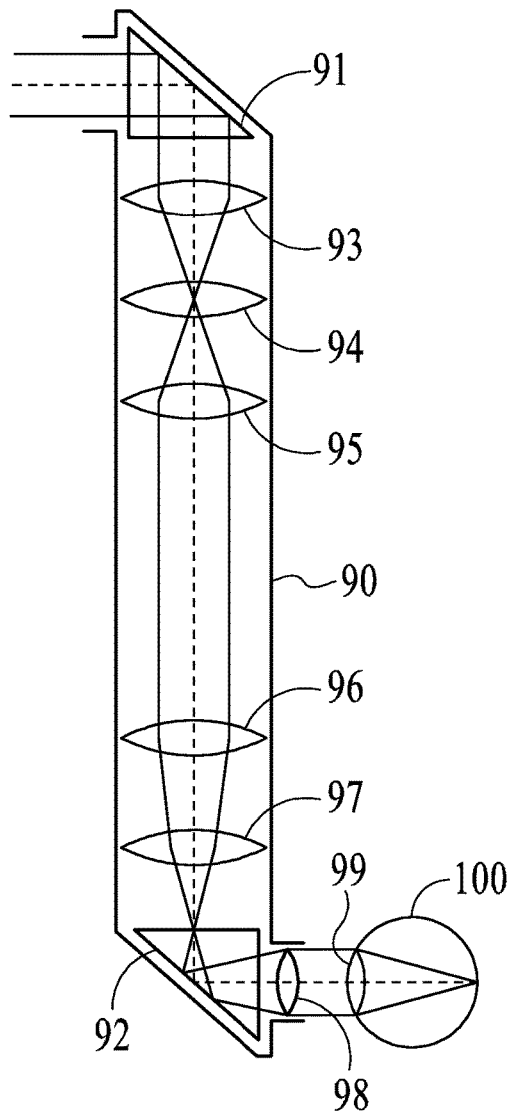

For example, FIG. 7 shows a periscope 70 implemented using a prism 71 and a prism 72 to focus an image at a camera lens location 73. For example, FIG. 8 shows a periscope 80 implemented using a prism 81, a prism 82, a lens 83, a lens 84, a lens 85, and a lens 86 to focus an image at a camera lens location 87. For example, FIG. 9 shows a periscope 90 implemented using a prism 91, a prism 92, a lens 93, a lens 94, a lens 95, a lens 96, a lens 97, a lens 98 and a lens 99 to focus an image at a camera lens location 100. Within the lenses in any of the implementations, magnification can be added, as desired, to obtain a desired image size.

The foregoing discussion discloses and describes merely exemplary methods and embodiments. As will be understood by those familiar with the art, the disclosed subject matter may be embodied in other specific forms without departing from the spirit or characteristics thereof. Accordingly, the present disclosure is intended to be illustrative, but not limiting, of the scope of the invention, which is set forth in the following claims.

What is claimed is:

1. A periscope module for an intra-oral camera, comprising:
   a mounting ring for mounting the periscope module over a camera lens of a mobile phone;
   a first periscope end for attachment to the mobile phone at the mounting ring;
   a second periscope end for capturing intra-oral images;
   a periscope tube connected between the first periscope end and the second periscope end; and,
   a light tube configured for attachment to a light source from the mobile phone, the light tube being configured to forward light into the first periscope end, the light exiting the second periscope end so as to provide illumination for capturing intra-oral images;
   wherein the light tube rotates around the first periscope end to allow configuration to be mounted at a location of the light source from the mobile phone.

2. A periscope module as in claim 1 wherein the mounting ring allows swiveling 360 degrees.

3. A periscope module as in claim 1 wherein the first periscope end includes a magnetic mount for attachment to the mobile phone.

4. A periscope module as in claim 1 wherein the first periscope includes a click dial connected to the light tube for locking in the rotation of the light tube at a specific location.

5. A periscope module as in claim 1 wherein the periscope tube includes a swivel point that allows 360-degree swiveling.

6. A periscope module as in claim 1 wherein material used to construct the periscope module include durable resins and metals that can withstand heat at or above at or above 132° C. (270° F.) used for sterilization and that can withstand chemical disinfection surface wipes.

7. An intra-oral camera, comprising:
   a mobile phone including a camera lens and a light source; and,
   periscope module for an intra-oral camera, comprising:
      a mounting ring for mounting the periscope module over the camera lens,
      a first periscope end for attachment to the mobile phone at the mounting ring,
      a second periscope end for capturing intra-oral images,
      a periscope tube connected between the first periscope end and the second periscope end, and
      a light tube configured for attachment to the light source, the light tube being configured to forward light into the first periscope end, the light exiting the second periscope end so as to provide illumination for capturing intra-oral images;
   wherein the light tube rotates around the first periscope end to allow configuration to be mounted at a location of the light source from the mobile phone.

8. An intra-oral camera as in claim 7 wherein the first periscope end includes a magnetic mount for attachment to the mobile phone.

9. An intra-oral camera as in claim 7 wherein the first periscope includes a click dial connected to the light tube for locking in the rotation of the light tube at a specific location.

10. An intra-oral camera as in claim 7 wherein the periscope tube includes a swivel point that allows 360-degree swiveling.

11. An intra-oral camera as in claim 7 wherein the mounting ring allows swiveling 360 degrees.

12. A camera attachment device, comprising:
   a mounting ring for mounting the camera attachment device over a camera lens of a mobile phone;
   a first periscope end for attachment to the mobile phone at the mounting ring;
   a second periscope end for capturing illuminated images;
   a periscope tube connected between the first periscope end and the second periscope end; and,
   a light tube configured for attachment to a light source from the mobile phone, the light tube being configured to forward light into the first periscope end, the light exiting the second periscope end so as to provide illumination for capturing illuminated images;
   wherein the light tube rotates around the first periscope end to allow configuration to be mounted at a location of the light source from the mobile phone.

13. A camera attachment device as in claim 12 wherein the first periscope end includes a magnetic mount for attachment to the mobile phone.

14. A camera attachment device as in claim 12 wherein the first periscope includes a click dial connected to the light tube for locking in the rotation of the light tube at a specific location.

15. A camera attachment device as in claim 12 wherein the periscope tube includes a swivel point that allows 360-degree swiveling.

16. A camera attachment device as in claim 12 wherein the mounting ring allows swiveling 360 degrees.

17. A camera attachment device as in claim 12 wherein material used to construct the camera attachment device include durable resins and metals that can withstand heat at or above at or above 132° C. (270° F.) used for sterilization and that can withstand chemical disinfection surface wipes.

* * * * *